(12) United States Patent
Confino et al.

(10) Patent No.: US 11,524,127 B2
(45) Date of Patent: Dec. 13, 2022

(54) SYSTEM AND METHOD FOR DELIVERY OF GAS TO A TISSUE

(71) Applicant: Beyond Air, Inc., Garden City, NY (US)

(72) Inventors: Hila Confino, Rehovot (IL); Steven A. Lisi, Garden City, NY (US); Rinat Kalaora, Rehovot (IL); Amir Avniel, Rehovot (IL); Matan Goldshtein, Rehovot (IL); Shay Yarkoni, Rehovot (IL)

(73) Assignee: Beyond Air, Inc., Garden City, NY (US)

( * ) Notice: Subject to any disclaimer, the term of this patent is extended or adjusted under 35 U.S.C. 154(b) by 0 days.

(21) Appl. No.: 17/620,696

(22) PCT Filed: Nov. 25, 2020

(86) PCT No.: PCT/IB2020/061149
§ 371 (c)(1),
(2) Date: Dec. 19, 2021

(87) PCT Pub. No.: WO2021/105900
PCT Pub. Date: Jun. 3, 2021

(65) Prior Publication Data
US 2022/0241522 A1 Aug. 4, 2022

Related U.S. Application Data

(60) Provisional application No. 63/090,345, filed on Oct. 12, 2020, provisional application No. 63/027,120, (Continued)

(51) Int. Cl.
*A61M 13/00* (2006.01)
*A61M 39/22* (2006.01)

(52) U.S. Cl.
CPC ........ *A61M 13/003* (2013.01); *A61M 39/223* (2013.01); *A61M 2202/0275* (2013.01);
(Continued)

(58) Field of Classification Search
CPC .. A61M 1/003; A61M 16/1015; A61M 16/20; A61M 16/201; A61M 2016/003;
(Continued)

(56) References Cited

U.S. PATENT DOCUMENTS 5,345,928 A 9/1994 Lindkvist
5,873,359 A 2/1999 Zapol et al.
(Continued)

FOREIGN PATENT DOCUMENTS

WO   WO 2008/095311   8/2008
WO   WO 2008/095312   8/2008
(Continued)

OTHER PUBLICATIONS

International Search Report and the Written Opinion dated Jul. 9, 2021 From the International Searching Authority Re. Application No. PCT/IB2020/061150.
(Continued)

*Primary Examiner* — Nathan R Price
*Assistant Examiner* — Courtney B Fredrickson
(74) *Attorney, Agent, or Firm* — Elmore Patent Law Group, P.C.; Joseph C. Zucchero; Carolyn S. Elmore

(57) ABSTRACT

A system for delivery of gas to a tissue, comprises: a first container containing the gas, an applicator having a distal end arranged to deliver the gas to the tissue, a second container containing a purging gas, and; and a flow control system for controlling flow of gas. The system also comprises a three-port valve having a first port for receiving the gas from the first container, a second port for receiving the purging gas from the second container, and a third port in
(Continued)

fluid communication with the applicator. The valve is switchable between a first state at which the first port fluidly connects to the third port, and a second state at which the second port fluidly connects to the third port.

21 Claims, 11 Drawing Sheets

Related U.S. Application Data filed on May 19, 2020, provisional application No. 62/985,611, filed on Mar. 5, 2020, provisional application No. 62/984,926, filed on Mar. 4, 2020, provisional application No. 62/982,817, filed on Feb. 28, 2020, provisional application No. 62/963,849, filed on Jan. 21, 2020, provisional application No. 62/939,975, filed on Nov. 25, 2019.

(52) U.S. Cl.
CPC ............... *A61M 2205/3334* (2013.01); *A61M 2205/3344* (2013.01); *A61M 2205/7536* (2013.01)

(58) Field of Classification Search
CPC .............. A61M 16/026; A61M 16/203; A61M 39/223; A61M 39/25; A61M 2039/229; Y10S 388/906; G05B 11/42; G05B 11/36; G05B 11/38; G05B 11/40; H02P 23/0004
See application file for complete search history.

(56) References Cited

U.S. PATENT DOCUMENTS

| | | | |
|---|---|---|---|
| 6,962,154 B2* | 11/2005 | Krebs | A61M 16/12 128/203.14 |
| 7,955,294 B2 | 6/2011 | Stenzler et al. | |
| 8,017,582 B2 | 9/2011 | Shinvan et al. | |
| 8,168,232 B2 | 5/2012 | Graham et al. | |
| 2002/0078958 A1* | 6/2002 | Stenzler | A61M 16/026 128/207.14 |
| 2004/0258772 A1 | 12/2004 | Otterbein et al. | |
| 2005/0004511 A1 | 1/2005 | Figley et al. | |
| 2007/0275100 A1 | 11/2007 | Miller | |
| 2008/0193566 A1 | 8/2008 | Miller et al. | |
| 2009/0205655 A1 | 8/2009 | Montgomery et al. | |
| 2013/0239962 A1 | 9/2013 | Goldstein | |
| 2018/0280654 A1* | 10/2018 | Borrello | A61M 16/0069 |

FOREIGN PATENT DOCUMENTS

| | | |
|---|---|---|
| WO | WO 2013/132500 | 9/2013 |
| WO | WO 2013/132503 | 9/2013 |
| WO | WO 2014/008490 | 1/2014 |
| WO | WO 2017/1055995 | 7/2014 |
| WO | WO 2016/168680 | 10/2016 |
| WO | WO 2021/105900 | 6/2021 |
| WO | WO 2021/105901 | 6/2021 |

OTHER PUBLICATIONS

International Search Report and the Written Opinion dated May 12, 2021 From the International Searching Authority Re. Application No. PCT/IB2020/061149.
Invitation to Pay Additional Fees dated May 3, 2021 From the International Searching Authority Re. Application No. PCT/IB2020/061150. (2 Pages).
Bonavida et al. "Nitric Oxide-Mediated Sensitization of Resistant Tumor Cells to Apoptosis by Chemo-Immunotherapeutics", Redox Biology, 6: 486-494, Available Online Aug. 18, 2015.
Confino et al. "Beyond Air® to Present New Nitric Oxide Data in an e-Poster Presentation at the North America Conference on Lung Cancer 2020 (NACLC 2020)", Globe News Wire, 7 P., Aug. 27, 2020.
Confino et al. "Gaseous Nitric Oxide at High Concentrations Is a Powerful Anti-Tumor Agent Both In-Vitro and In-Vivo", AACR, Poster, Jun. 2020.
Confino et al. "Nitric Oxide Lung Cancer Active Vaccination", 2020 North America Conference on Lung Cancer, #NACLC20, Worldwide Virtual Event, Oct. 16-17, 2020, Slide Show, 14 P., Oct. 16, 2020.
Confino et al. "Nitric Oxide Tumor Ablation Stimulates an Anti-Tumor Immune Response in Mice", AACR, American Association for Cancer Research, AACR Virtual Special Conference on Tumor Immunology and Immunotherapy, Israel, Oct. 19-20, 2020, Power Point Presentation, 15 P., Oct. 19, 2020.
El-Naa et al. "Sildenafil Potentiates the Antitumor Activity of Cisplatin by Induction of Apoptosis and Inhibition of Proliferation and Angiogenesis", Drug Design, Development and Therapy, 10: 3661-3672, Published Online Nov. 16, 2016.
Huerta "Nitric Oxide for Cancer Therapy", Future Science, 1(1): FSO44-1-FSO44-9, Aug. 1, 2015.
Keisari et al. "Activation of Local and Systemic Anti-Tumor Immune Responses by Ablation of Solid Tumors With Intratumoral Electrochemical or Alpha Radiation Treatments", Cancer Immunology, Immunotherapy, 63(1): 1-9, Published Online Aug. 17, 2014.
Knavel et al. "Tumor Ablation: Common Modalities and General Practices", Techniques in Vascular and Interventional Radiology, 16(4): 192-200, Dec. 2013.
Lin et al. "Non-Thermal Plasma as a Unique Delivery System of Short-Lived Reactive Oxygen and Nitrogen Species for Immunogenic Cell Death in Melanoma Cells", Advanced Science, 6(6): 1802062-1-1802062-15, Jan. 28, 2019.
Nath et al. "Nitric Oxide-Releasing Aspirin Suppresses NF-KB Signaling in Estrogen Receptor Negative Breast Cancer Cells In Vitro and In Vivo", Molecules, 20(7): 12481-12499, Jul. 9, 2015. 2015.
Ning et al. "Novel Nitric Oxide Generating Compound Glycidyl Nitrate Enhances the Therapeutic Efficacy of Chemotherapy and Radiotherapy", Biochemical and Biophysical Research Communications, 447(3): 537-542. Available Online Apr. 13, 2014.
Rizi et al. "Nitric Oxide: The Forgotten Child of Tumor Metabolism", Trends in Cancer, 3(9): 659-672, Published Online Aug. 18, 2017.
Schairer et al. "The Potential of Nitric Oxide Releasing Therapies as Antimicrobial Agents", Virulence, 3(3): 271-279, Published Online May 1, 2012.
Seabra et al. "Nitric Oxide Donors for Prostate and Bladder Cancers: Current State and Challenges", European Journal of Pharmacology, 826: 158-168, Published Online Mar. 1, 2018.
Slovak et al. "Immuno-Thermal Ablations—Boosting the Anticancer Immune Response", Journal for ImmunoTherapy of Cancer, 5(1): 78-1-78-15, Oct. 17, 2017.
Srivatsan et al. "Allogeneic Tumor Cell Vaccines. The Promise and Limitations in Clinical Trials", Human Vaccines & Immunotherapeutics, 10(1): 52-63, Published Online Sep. 24, 2013.
Vannini et al. "The Dual Role of iNOS in Cancer", Redox Biology, 6: 334-343, Available Online Aug. 24, 2015.
Weyerbrock et al. "Growth Inhibition and Chemosensitization of Exogenous Nitric Oxide Released From NONOates in Glioma Cells In Vitro: Laboratory Investigation", Journal of Neurosurgery, 110(1): 128-136, Jan. 2009.
International Preliminary Report on Patentability dated Jun. 9, 2022 From the International Bureau of WIPO Re. Application No. PCT/IB2020/061149. (8 Pages).
International Preliminary Report on Patentability dated Jun. 9, 2022 From the International Bureau of WIPO Re. Application No. PCT/IB2020/061150. (15 Pages).

\* cited by examiner

SYSTEM AND METHOD FOR DELIVERY OF GAS TO A TISSUE

RELATED APPLICATIONS

This application is a National Phase of PCT Patent Application No. PCT/IB2020/061149 having International filing date of Nov. 25, 2020, which claims the benefit of priority under 35 USC § 119(e) of U.S. Provisional Patent Application Nos. 62/984,926, filed on Mar. 4, 2020, 62/939,975, filed on Nov. 25, 2019, 62/963,849, filed on Jan. 21, 2020, 62/982,817, filed on Feb. 28, 2020, 62/985,611, filed on Mar. 5, 2020, 63/027,120, filed on May 19, 2020, and 63/090,345, filed on Oct. 12, 2020. The contents of the above applications are all incorporated by reference as if fully set forth herein in their entirety.

PCT Patent Application No. PCT/IB2020/061149 having International filing date of Nov. 25, 2020 is also related to co-filed PCT entitled "METHODS EMPLOYING GASEOUS NITRIC OXIDE FOR INHIBITING TUMOR GROWTH", the contents of which are incorporated herein by reference in their entirety.

FIELD AND BACKGROUND OF THE INVENTION

The present invention, in some embodiments thereof, relates to medical equipment and, more particularly, but not exclusively, to a system and method for delivery of gas, e.g., gaseous Nitric Oxide (NO) to a tissue.

In 2018, about 18.1 million new cases of cancer and 9.6 million deaths from cancer have been reported worldwide (Ferlay, J. et al. Estimating the global cancer incidence and mortality in 2018: GLOBOCAN sources and methods. Int. J. cancer 144, 1941-1953 2019). Only in the US, there are estimated 1,762,450 cancer cases and 606,880 cancer deaths since Jan. 2019 (Siegel, R. L., Miller, K. D. & Jemal, A. Cancer statistics, 2019. CA. Cancer J. Clin. 69, 7-34).

In order to treat cancer effectively, efficient removal of the primary tumor mass and prevention of secondary tumor growth, and eradication of metastatic cells must be achieved. Furthermore, significant prevention of recurrence of cancer growth can be achieved by generation of anti-cancer immune responses.

Surgical excision of tumors is a widely employed therapeutic modality for the treatment of cancer, in which the primary goal is the complete eradication of local and regional tumor. This involves removal of adequate margins of normal tissue surrounding the tumor, and radical wide excision in order to prevent local recurrence. It is recognized (Eilber F R. Principles of cancer surgery. In: Cancer Treatment, Haskell C M, (ed.) 5th ed., pp. 47, W.B. Saunders Co. Philadelphia, 2001) that surgical treatment of malignant neoplasms remains limited. Another efficient anti-cancer remedy is chemotherapy (Haskell C M. Principles of cancer chemotherapy. In: Cancer Treatment, Haskell C M, (ed.) 5th ed. pp. 62-86, W.B. Saunders Co. Philadelphia, 2001).

An alternative treatment approach is the engagement of the host immune system to react against tumor-associated antigens. An efficient immune-stimulating technique is ablation of the tumor that results in the release of tumor antigens and stimulates/triggers the immune system (Keisari, Y., Hochman, I., Confino, H., Korenstein, R. & Kelson, I. Activation of local and systemic anti-tumor immune responses by ablation of solid tumors with intratumoral electrochemical or alpha radiation treatments. Cancer Immunol. Immunother. 63, 1-9; 2014). Tumor ablation is a minimally invasive technique that is commonly used in the treatment of solid tumors in the liver, kidney, bone, and lung. Within the classification of tumor ablation, there are several modalities used worldwide, for example radiofrequency and cryoablation (Knavel, E. M. & Brace, C. L. Tumor ablation: common modalities and general practices. Tech. Vasc. Interv. Radiol. 16, 192-200; 2013).

Local and in-situ tumor ablation methods were shown to enhance anti-tumor immune responses resulting in the destruction of residual malignant cells in primary tumors and distant metastases (Keisari, Y., Hochman, I., Confino, H., Korenstein, R. & Kelson, I. Activation of local and systemic anti-tumor immune responses by ablation of solid tumors with intratumoral electrochemical or alpha radiation treatments. Cancer Immunol. Immunother. 63, 1-9; 2014). Notably, in contrast to surgical resection, ablation differs in that the tumor material is left in the tumor site/body. Even with the bulk of the tumor destroyed, antigenic remnants persist. This aspect of ablation is responsible for its ability to trigger a systemic antitumor immune response where surgical resection would not. Thus, this anti-tumor immune response triggered by the tumor ablation technique can fight remainder cancer cells at the primary tumor site as well as metastasis (Slovak, R., Ludwig, J. M., Gettinger, S. N., Herbst, R. S. & Kim, H. S. Immuno-thermal ablations—boosting the anticancer immune response. J. Immunother. Cancer 5, 78; 2017).

SUMMARY OF THE INVENTION

Surgical techniques are effective only in the area of the primary tumor or regional lymphatics and do not affect neoplasms located outside the operative field. Furthermore, due to anatomic location, many tumors cannot be treated by surgical resection because removal of an adequate margin of normal tissue cannot be achieved. Also, surgical treatment is often not an option for tumors intimately involving major blood vessels or essential organs. Additionally, many patients present problematic medical histories, such as cerebrovascular or cardiovascular accidents, or uncontrolled diabetes, rendering them poor surgical candidates because of their high postoperative mortality rate. Also, in many cases, tumor excision cannot be performed without causing unacceptable levels of impairment of physiologic functions or cosmetic damage.

Chemotherapeutic agents often cause severe and unacceptable side-effects, such as bone marrow and lymphoid organ damage resulting in immunosuppression, thereby rendering subjects highly vulnerable to lethal opportunistic infections, as well as various other types of organ toxicities. Thus, the use of cytotoxic drugs is limited only to tolerated doses.

Considering the disadvantages of the current treatments for cancer, the Inventors searched for an improved technique for treating, controlling or preventing tumor development. Some embodiments of the present invention administer gaseous NO (gNO) to treat tumors. The documents cited in the previous section fail to teach or imply use of high doses of nitric oxide, fail to teach injecting or exposing a solid tumor or metastasis to high doses of nitric oxide. While delivery of gNO through tumor tissues is challenging, in view of the reactivity, corrosiveness, toxicity, and unstableness, the Inventors have successfully devised a system for delivery of gas, particularly, gNO, to a tissue.

The system of the present embodiments can effectively administer gaseous nitric oxide to treat tumors. Compared to conventional techniques, the system of the present embodiments is more targeted in treating tumors, particularly cancerous cells in vivo. The system of the present embodiments can effectively deliver gNO in treatment regimes, and can deliver gNO to target sites, with minimal damage, and preferably without damaging, healthy adjacent host cells, optionally and preferably while simultaneously identifying the target site and evaluating the effect of gNO administration thereto.

According to some embodiments of the invention the present invention there is provided a system for delivery of gas to a tissue. The system comprises: a first container containing the gas; an applicator having a distal end arranged to deliver the gas to the tissue; a second container containing a purging gas; a three-port valve having a first port for receiving the gas from the first container, a second port for receiving the purging gas from the second container, and a third port in fluid communication with the applicator, the valve being switchable between a first state at which the first port fluidly connects to the third port, and a second state at which the second port fluidly connects to the third port; and a flow control system for controlling flow of gas exiting the third port.

According to some embodiments of the invention the applicator and the first container are disposable.

According to some embodiments of the invention the system comprises a suctioning device arranged to apply suction at a vicinity of the distal end of the applicator to withdraw excess gas exiting the distal end.

According to some embodiments of the invention the system comprises a filter, for filtering the withdrawn excess gas.

According to some embodiments of the invention the flow control system comprises an orifice and a valve. According to some embodiments of the invention the valve of the flow control system is a solenoid valve.

According to some embodiments of the invention the flow control system comprises a flow controller and a flow limiter for limiting flow rate of the gas before entering the flow controller.

According to some embodiments of the invention the system comprises an adjustable pressure regulator, in fluid communication with the third port of the valve, and being configured for maintaining a pressure which is below a predetermined threshold when the valve assumes the first state, and a pressure which is above the predetermined threshold when the valve assumes the second state.

According to some embodiments of the invention the system comprises a computerized controller for automatically controlling the flow control system, according to at least one of: a predetermined gas flow rate, a predetermined total amount of the gas flowing through the flow control system, and a predetermined total amount of time in which the gas flows through the flow control system.

According to some embodiments of the invention the flow control system comprises a digital flow controller configured for controlling flow in closed loop according to a pseudo-derivative tuning coefficient and a proportional tuning coefficient, and wherein the computerized controller is configured to receive via an user interface input flow rate of the gas, and to automatically select the tuning coefficients based on the input.

According to some embodiments of the invention the digital flow controller is configured for controlling the flow in closed loop also according to an integral tuning coefficient, and the computerized controller is configured to automatically select the integral tuning coefficient based on the input.

According to some embodiments of the invention the computerized controller is configured to select for the proportional tuning coefficient a value which is higher for lower input flow rates than for higher input flow rates.

According to some embodiments of the invention the computerized controller is configured to select for the pseudo-derivative tuning coefficient a value which is lower for lower input flow rates than for higher input flow rates.

According to some embodiments of the invention the system is installed in a treatment room, and comprises an arrangement of sensors distributed in the treatment room and configured for sensing the gas and issue an alert signal when a level of the gas is above a respective predetermined threshold.

According to some embodiments of the invention the system is installed in a treatment room, and comprises an arrangement of sensors distributed in the treatment room for sensing the gas, wherein the computerized controller is configured to receive sensing signals from the sensors and issue an alert signal when a level of the gas is above a respective predetermined threshold.

According to some embodiments of the invention the computerized controller and the applicator are at the same room.

According to some embodiments of the invention the computerized controller and the applicator are different rooms.

According to some embodiments of the invention the computerized controller is configured to control the three-port valve to perform purging in multiple cycles.

According to an aspect of some embodiments of the present invention there is provided a method for delivery of gas to a tissue, the method comprises: in the system as delineated above and optionally and preferably as further detailed below: connecting the first container to the valve; switching the valve to the first state, thereby delivering the gas to the tissue; disconnecting the applicator and the first container; and switching the valve to the second state, thereby purging at least the flow control system.

According to some embodiments of the invention the method comprises apply suction at a vicinity of the distal end of the applicator to withdraw excess gas exiting the distal end.

According to some embodiments of the invention the method is executed by an operator, and comprises delivering air or oxygen or oxygen-enriched air to the operator.

According to some embodiments of the invention method comprises delivering air or oxygen or oxygen-enriched air to the subject.

According to some embodiments of the invention the delivering is by a mask.

According to some embodiments of the invention the subject is a mammal.

According to some embodiments of the invention the subject is a human.

According to some embodiments of the invention the purging comprises applying multiple pressurize and depressurize cycles, followed by continuous flow of the purging gas.

According to some embodiments of the invention for at least one of the cycles, a depressurizing part of the cycle comprises applying vacuum.

According to some embodiments of the invention the first container has a volume of less than 100 cc.

According to some embodiments of the invention a gas pressure in the first container is less than 10 bar.

According to some embodiments of the invention the second container has a volume which is larger than a volume of the first container.

According to some embodiments of the invention a gas pressure in the second container is at According to some embodiments of the invention the gas is gNO.

According to some embodiments of the invention a concentration of the gas in the first container is from about 1,000 ppm to about 1,000,000 ppm.

According to some embodiments of the invention the purging gas is nitrogen or argon.

According to an aspect of some embodiments of the present invention there is provided a gas delivery device, which comprises a disposable container filled with gNO at a pressure of less than 10 bar, and having a gas outlet, the disposable container having a volume of less that 100 cc. The gas delivery device optionally and preferably comprises a valve, mounted on the outlet.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
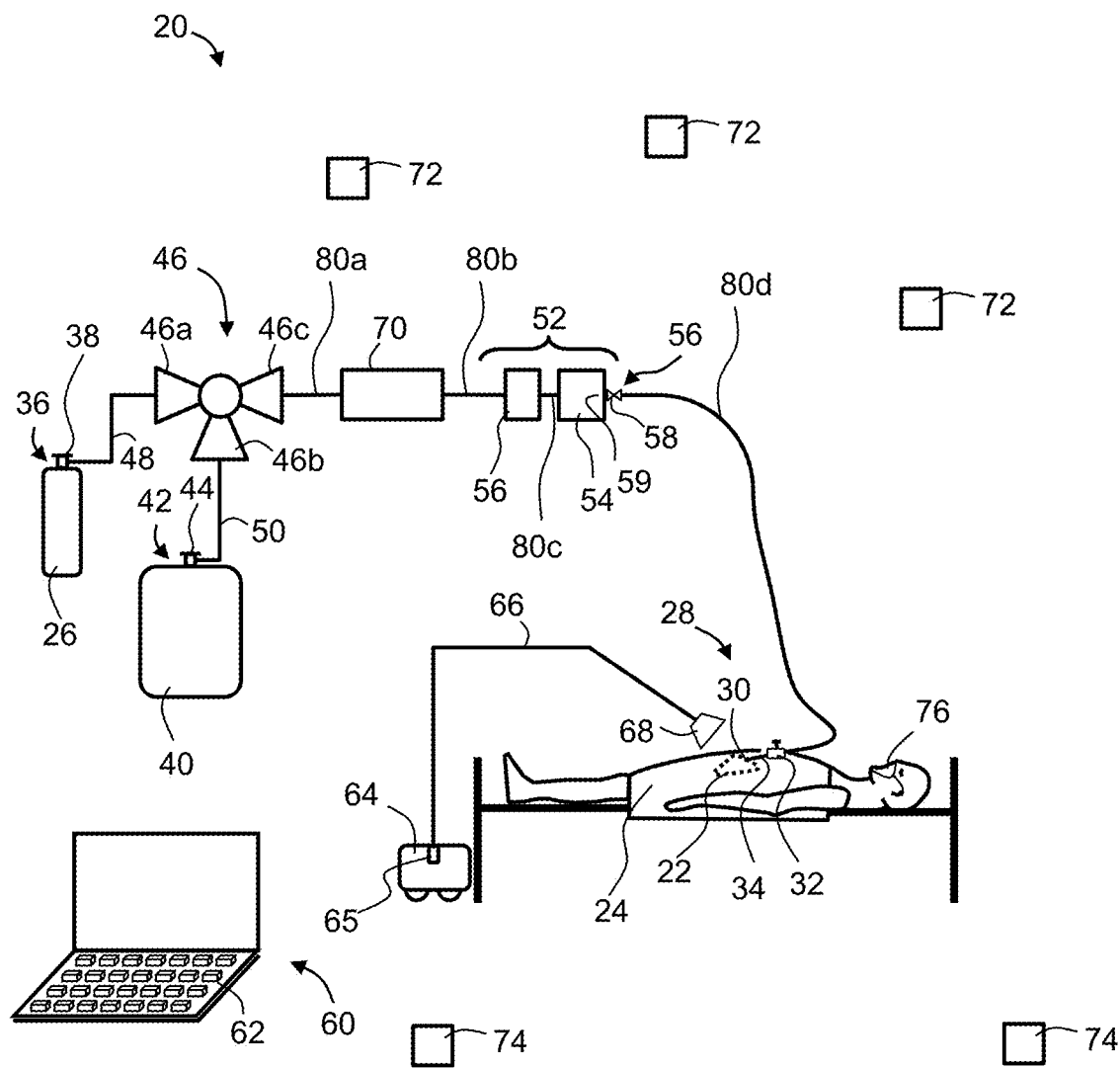
FIG. 1 is a schematic illustration of a system for delivery of gas to a tissue of a subject, according to some embodiments of the present invention.

The present invention, in some embodiments thereof, relates to medical equipment and, more particularly, but not exclusively, to a system and method for delivery of gas, e.g., gaseous Nitric Oxide (NO) to a tissue.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 illustrates a system 20 for delivery of gas to a tissue 22 of a subject 24, according to some embodiments of the present invention. The subject 24 is optionally and preferably a mammalian subject, more preferably a human subject. The tissue 22 is typically a tumor or a metastasis, and the gas is delivered for the purpose of treating the tumor or metastasis. In some embodiments of the present invention a malignant tumor.

Typical tumors treatable by system 20 include, but are not limited to, breast tumor, brain tumor, neuroblastoma, thyroid gland tumor, gestational trophoblastic tumor, uterine sarcoma, carcinoid tumor, colon carcinoma, esophageal carcinoma, hepatocellular carcinoma, liver carcinoma, lymphoma, plasma cell neoplasm, mesothelioma, thymoma, alveolar soft-part sarcoma, angiosarcoma, epithelioid sarcoma, extraskeletal chondrosarcoma, fibrosarcoma, leiomyosarcoma, liposarcoma, malignant fibrous histiocytoma, malignant hemangiopericytoma, malignant mesenchymoma, malignant schwannoma, synovial sarcoma, melanoma, neuroepithelioma, osteosarcoma, leiomyosarcoma, Ewing sarcoma, osteosarcoma, rhabdomyo-sarcoma, hemangiocytoma, myxosarcoma, mesothelioma (e.g., lung mesothelioma), granulosa cell tumor, thecoma cell tumor and Sertoli-Leydig tumor.

System 20 can therefore be used to treat many types of cancers, such as, but not limited to, vaginal cancer, vulvar cancer, cervical cancer, endometrial cancer, ovarian cancer, rectal cancer, salivary gland cancer, laryngeal cancer, nasopharyngeal cancer, many lung metastases and acute or chronic leukemia (e.g., lymphocytic, Myeloid, hairy cell).

The gas is optionally and preferably gNO, but other therapeutic gases are also contemplated.

System 20 comprises a first container 26 containing the gas, and an applicator 28 having a distal end 30 arranged to deliver the gas to the tissue 22. The gas is delivered to applicator 28 via a gas flow line shown at 80d. The applicator 28 can be of any type that has an outlet through which a flow of gas can exit. Typically, but not necessarily, applicator 28 is a transcutaneous device, e.g., a cannula 32 that ends in a needle 34 or a sprayer. The needle 34 can be any suitable needle for delivering the gas (e.g., gNO) including, but not limited to, a perforated spray needle, non-perforated and non-spray needle, umbrella needle, or other needles. The needle can optionally be nano size, micron size or macro size needles. Also contemplated are embodiments in which applicator 28 is configured for spraying, or otherwise exposing the tissue to the gas, in an open or closed container (e.g., a container sized to conform to the contours of the tumor), or to fill a space or a physiological cavity containing one or more tumors with the gas. Representative examples of applicators suitable for use as applicator 28 are provided in the Examples section that follows.

First container 26 typically comprises an outlet 36 and a valve 38 mounted thereon. First container 26 is optionally and preferably disposable. This is particularly advantageous when the gas is toxic, as in the case of gNO, so that the disposable container can be connected to system 20 immediately before treatment, and disposed immediately after treatment, thus reducing the time at which the toxic substance is in the treating room. In various exemplary embodiments of the invention the volume of container 26 is sufficient small (e.g., less than 100 cc, or less than 90 cc, or less than 80 cc, or less than 70 cc, or less than 60 cc or less than 50 cc) so that the amount of gas in container is not more than the typical gas dose to be delivered to the tissue. This is particularly advantageous when the gas is toxic, as in the case of gNO, because in the event of undesired leakage of the gas into the treating room, the total amount of gas that can be leaked is small, compared to the size of the room, thus reducing the risk of inhaling a hazardous concentration of the gas by the subject 24 or medical personnel.

For example, when the gas is gNO, the immediately dangerous to life or health (IDLH) concentration is 100 ppm, and so the amount of gNO in container 26 is preferably less than 1/10000 of a typical volume of a treating room, which is typically from about 40,000 liters to about 60,000. Thus, the volume of container 26 can be from about 10 cc to about 60 cc, and it can be filled with the gas at a volumetric concentration of from thousand ppm to several hundred-thousands ppm (e.g., 1,000-1,000,000 ppm), where "ppm" (parts per million) refers to the fraction (e.g., volumetric fraction) of the gas in a gas carrier. The gas carrier can be air, and preferably an inert gas such as nitrogen or argon, preferably nitrogen. In embodiments, the volume of first container 26 is from about 10 cc to about 3.5 L.

The gas pressure in container 26 is preferably low, e.g., less than 5 bar, e.g., from about 1 bar to about 5 bar. Alternatively, the gas pressure in container 26 can be higher (e.g., from about 5 bar to about 20 bar).

Thus, the first container 26 can comprise from about 1,000 ppm to 1,000,000 ppm of the gas, or any intermediate subrange therebetween, for example, from about 1,000 ppm to about 200,000 ppm, or from about 1,000 ppm to about 100,000 ppm, preferably from about 10,000 ppm to about 500,000 ppm, or from about 10,000 ppm to about 200,000 ppm, or from about 10,000 ppm to about 100,000 ppm, or from about 20,000 ppm to about 100,000 ppm, or from about 25,000 ppm to about 100,000 ppm, or from about 25,000 ppm to about 75,000 ppm, or from about 10,000 ppm to about 50,000 ppm, or from about 50,000 ppm to about 100,000 ppm, including any intermediate values and subranges between any of the foregoing, or is about 50,000 ppm.

System 20 can further comprise a second container 40 containing a purging gas, and having an outlet 42 and a valve 44 mounted thereon. Preferably, the purging gas is non-hazardous to the subject, more preferably an inert gas, such as, but not limited to, nitrogen or argon. As the purging gas is non-hazardous, the volume of the second container 40 can be larger (e.g., 10 times or 100 times or 1000 times larger) than the volume of container 26. The gas pressure in container 40 is preferably sufficiently high to ensure efficient purging. Typically, the pressure in container 40 is at least 10 bar, or at least 20 bar, or at least 30 bar, or at least 40 bar, or at least 50 bar, e.g., from about 10 bar to about 200 bar.

Containers 26 and 40 are in fluid communication with a multi-port valve 46. In the schematic illustration of FIG. 1, which is not to be considered as limiting, valve 46 is embodied as a three-port valve having a first port, 46a, a second port 46b and a third port 46c. Valve 46 can be of any type, such as, but not limited to, a ball valve, a gate valve, a plunger valve, a butterfly valve or the like. Port 46a is typically in fluid communication with first container 36, port 46b is typically in fluid communication with second container 40, and port 46c is typically in fluid communication with applicator 28. In various exemplary embodiments of the invention the fluid communications between container 26 and port 46a, and between container 40 and port 46b are direct, namely that there are gas delivery lines 48 and 50 that respectively connect the containers 26 and 40 with the ports 46a and 46b, and there is no additional elements that interact with the respective gas along these lines. The connection of line 48 and optionally also of line 50 to the respective ports of valve 46 is preferably of the fast connection type.

Valve 46 is switchable between a first state at which port 46a fluidly connects to port 46c, and a second state at which port 46b fluidly connects to port 46c. During treatment, valve 46 assumes the first state, and the gas flow from container 26 to the applicator 28 and into the tissue 22. Between treatment sessions, more preferably before and after each treatment session, applicator 28 and optionally and preferably also container 26 are removed from system 20, and a purge step is executed by switching valve 46 to its second state, allowing the purging gas to enter the other components of system 20. The purging using the purging gas can contain one or several pressurizing and depressurizing cycles. The purging can, in some embodiments of the present invention, employ vacuum, as further detailed hereinbelow.

System 20 optionally and preferably also comprises a flow control system 52 for controlling the flow of gas exiting port 46c of valve 46. The gas is delivered to flow control system by a gas flow line shown 80b. Flow control system 52 is typically operated during treatment session and is switched off during the purge steps, but operating control system 52 during the purge steps is also contemplated. In embodiments, the flow control system 52 is configured, to deliver the gas for a time period of from about 1 second to about 60 minutes. In embodiments, flow control system 52 is configured to deliver a predetermined amount (volume and/or mass) of gas. In embodiments, flow control system 52 is configured to apply treatment in cycles. For example, flow control system 52 can pause the delivery after a predetermined amount of time and/or after a predetermined amount (volume and/or mass) of the gas has been delivered, and then, after a predetermined time interval, resume the delivery.

In some embodiments of the present invention flow control system 52 comprises an orifice 59 controlled by a valve 58, such as, but not limited to, an on/off valve, which in some embodiments of the present invention can be a solenoid valve.

In some embodiments of the present invention flow control system 52 comprises a flow controller 54 and a flow limiter 56. The gas flow from flow limiter 56 to flow controller 54 via a gas flow line shown at 80c.

Flow limiter 56 serves for limiting the flow rate (typically the volumetric flow rate) of the gas before entering flow controller 54. For example, flow limiter 56 can be an analogue flow controller, equipped with a knob (not shown, see FIGS. 3B and 3C) for setting an upper limit on the flow rate of the gas passing through limiter 56. The flow limiter can in some embodiments of the present invention include an orifice of a diameter selected to limit the maximum flow, thus serving as a flow restrictor. Typically, flow limiter 56 limit the gas flow rate to a value of from about 0.01 liters per minute (LPM) to about 0.15 LPM, more preferably from about 0.011 liters per minute (LPM) to about 0.11 LPM. Suitable devices for use as flow limiter 56 include the analogue flow controller VAF-G2-01L series, and the flow restrictor 6LV-4-VCR-6-DM series, both commercially available from Swagelok, USA.

Flow controller 54 is optionally and preferably a digital flow controller, more preferably a Proportional-Derivative (PD) controller or a Proportional-Integral-Derivative (PID) controller, configured for controlling the flow through controller 54 in closed loop. The closed loop control of controller 54 can be according to tuning coefficients. Specifically, controller 54 receives, as input, a value of the flow rate, and repeatedly measures the flow rate at its outlet 56. Controller 54 calculates the difference between the measured value of the flow rate and the input value of the flow rate, and then calculates a control signal using the calculated difference. The control signal is used by controller 54 to operate a valve 58 at its outlet 56. The control signal is optionally and preferably calculated as a weighted sum of the calculated difference, the time-derivative of the calculated difference, and optionally also the time-integral of the calculated difference. The weight of the calculated difference in the control signal is referred to as a proportional tuning coefficient, the weight of the time-derivative of the calculated difference in the control signal is referred to as the pseudo-derivative tuning coefficient and, the weight of the time-integral (when computed) of the calculated difference in the control signal is referred to as the integral tuning coefficient.

In some embodiments of the present invention the value of the proportional tuning coefficient is higher for lower input flow rates than for higher input flow rates, and in some embodiments of the present invention the value of the differential tuning coefficient is lower for lower input flow rates than for higher low input flow rates. Representative preferred ranges for the proportional (P) and pseudo-derivative (D) tuning coefficients, for several input flow rates are provided in Table 1, below.

TABLE 1

| Input flow rate [LPM] | P | D [minute$^{-1}$] |
|---|---|---|
| 0.05 | 2000-3000 | 200-250 |
| 0.25 | 500-1000 | 300-400 |
| 0.5 | 300-500 | 400-600 |
| 0.75 | 250-350 | 500-700 |

In some embodiments of the present invention system 20 comprises a computerized controller 60 having a circuit configured to automatically control flow control system 52. For clarity of presentation, control lines from and to computerized controller 60 are not illustrated. In some embodiments of the present invention computerized controller 60 is at the treatment room (the same room with the applicator 28). More preferably computerized controller 60 is outside the treatment room (controller 60 and applicator are at different rooms). The advantage of this embodiment, is that it reduces the risk of exposure to the gas by the medical practitioner accessing and/or operating computerized controller 60.

Computerized controller 60 controls flow control system 52 according to a predetermined gas flow rate, and/or a predetermined total amount of the gas flowing through system 52, and/or a predetermined total amount of time in which the gas flows through system 52. Computerized controller 60 can comprise a dedicated circuitry and/or a general purpose computer, configured for receiving data and executing the operations described below. Computerized controller 60 can also include a user interface 62 for receiving input from the operator. For example, controller 60 can receive via user interface 62 an input flow rate of the gas, and automatically select the tuning coefficients (e.g., according to Table 1, above, or according to any other scenario).

Controller 60 can also receive via user interface 62 an input dose of the gas to be delivered to the subject 24 and transmits a control signal to flow control system 52 to ensure that the total amount of delivered gas does not exceeds the input dose. For example, controller 60 can receive from the digital flow controller 54 a monitoring signal pertaining to the amount of gas that exits outlet 56 and transmit a stop signal to system 52 once the amount of gas has reached the dose. In some optional embodiments of the invention computerized controller 60 also controls one or more of valves 46 and 38, to ensure that the amount of gas delivered does not exceeds the input dose.

In some embodiments of the present invention system 20 comprises a suctioning device 64 arranged to apply suction at a vicinity of the distal end 30 of applicator 28 to withdraw excess gas exiting distal end 30. The suctioning of the gas can be done in a pulsed or continuous manner. Device 64 preferably has an adjustable arm 66 having a suction inlet 68 at its end. The length and/or orientation of arm 66 can be adjusted by the medical partitioned before beginning the treatment session such that the suction inlet 68 is at close proximity to the distal end 30 of applicator 68. In use, excess gas that does not enter tissue 22 is sucked into suction inlet 68 instead of being released to the environment. The withdrawn gas that enters the suction inlet 68 is optionally and preferably passed through a filter 65 selected to remove hazardous gas components such as gNO and $NO_2$. For example, filter 65 can be a Sodalime or alkaline activated carbon filter. Typically, a gas flow line (not shown) is mounted on or embedded in arm 66. Filter 65 can be installed in device 64, as illustrated in FIG. 1, or alternatively at a location along the gas flow line mounted on or embedded in arm 66. The gas withdrawn by device 64 can be evacuated to the medical center pipe (not shown).

In some embodiments of the present invention computerized controller 60 is configured also to control suctioning device 64. In these embodiments computerized controller 60 activates device 64 before the beginning of the treatment session, and deactivates it after the end of the treatment session.

It is to be understood that while FIG. 1 illustrates a single suction inlet 68, the present embodiments contemplate a plurality of suction inlets. For example, device 64 can include multiple suction inlets. Alternatively or additionally, system 20 can include a plurality of suctioning devices, each comprising one or more suction inlets.

In some embodiments of the present invention system 20 comprises an adjustable pressure regulator 70, in fluid communication with port 46*c* of valve 46. The gas flows from port 46*c* to regulator 70 via a gas flow line shown at 80*a*. Pressure regulator 70 is preferably configured for maintaining a pressure which is below a predetermined threshold when valve 46 assumes its first state (treatment session), and a pressure which is above the predetermined threshold when valve 46 assumes its second state (between treatment sessions). A typical pressure threshold employed by pressure regulator 70 is, without limitation from about 2 bars to about 5 bars. Pressure regulator 70 typically includes one or more pressure gauge devices (not shown, see FIGS. 3B and 3C) for providing indication regarding the gas pressure downstream and/or upstream the regulator 70.

System 20 is typically installed in a treatment room. Optionally, but not necessarily, the treatment room is sealed to the environment so as to ensure that the gas (e.g., gNO) does not leak out of the room. In various exemplary embodiments of the invention system 20 comprises an arrangement of sensors 72 distributed in the treatment room for sensing the gas. Sensors 72 are optionally and preferably configured for generating an alert signal when the level of the gas is above a respective predetermined threshold. In some embodiments of the present invention, the arraignment also include sensors 74 configured for sensing one or more reaction products of the gas. Sensors 74 are optionally and preferably configured for generating an alert signal when the level of the reaction product is above a respective predetermined threshold, which may be the same as the aforementioned threshold. For example, when the gas is gNO, sensors 74 can be configured for sensing $NO_2$, which is the reaction product of gNO with oxygen. The vertical locations of sensors 72 and 74 can be selected based on the specific density of the gas and reaction product to be sensed. For example, when sensors 72 sense gNO and sensors 74 sense $NO_2$, sensors 72 can be distributed at the upper part of the room, and when sensors 74 sense $NO_2$, sensors 74 can be distributed at the lower part of the room.

The predetermined threshold can be, for example, a value from about 25 ppm to about 100 ppm. Suitable sensors for sensing gNO are commercially available from, for example, Honeywell analytics, United Kingdom, and WatchGas, The Netherlands.

In some embodiments of the present invention computerized controller 60 receives sensing signals from sensors 72 and/or 74 issues an alert signal when the level of the gas (e.g., gNO) and/or reaction product (e.g., $NO_2$) is above the respective predetermined threshold.

Figure 2:
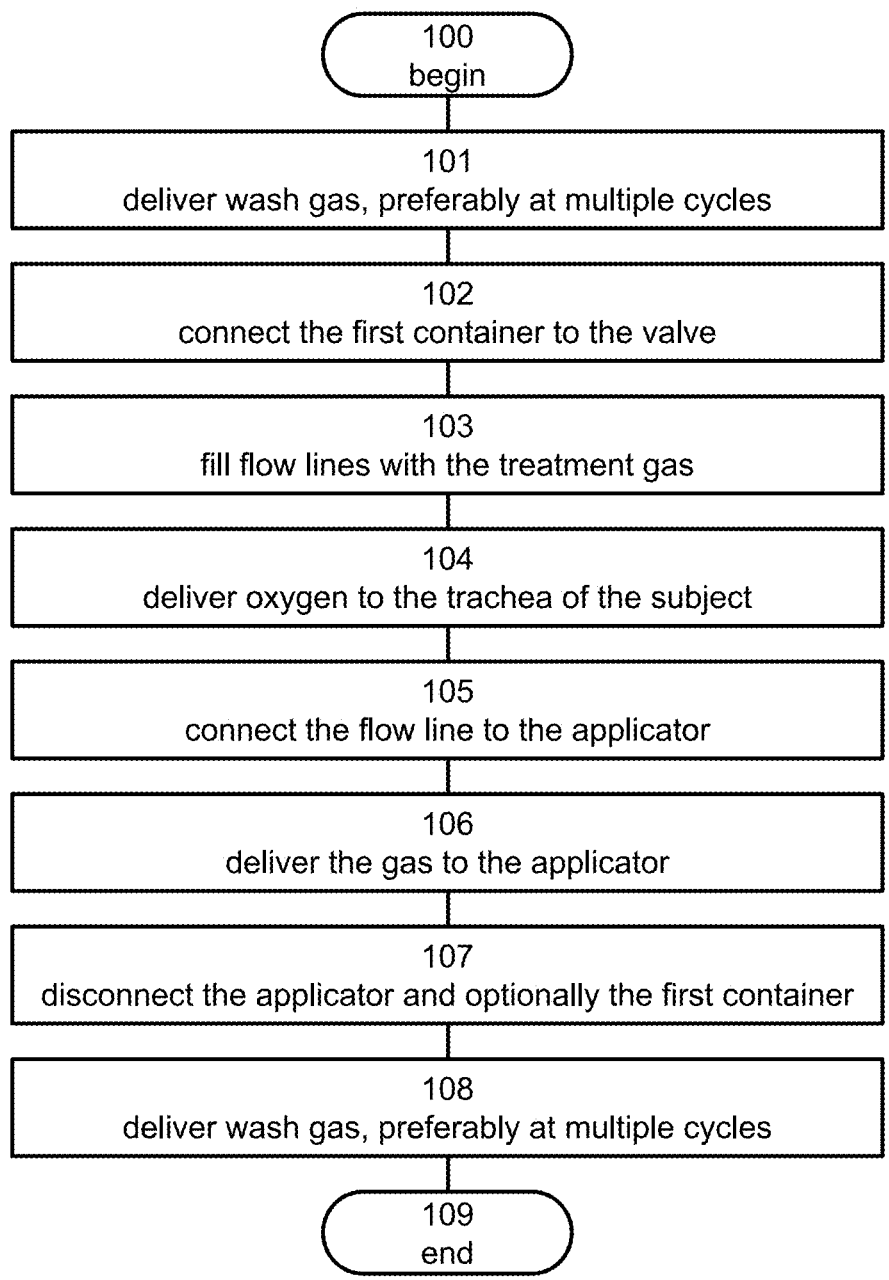
FIG. 2 is a is a flowchart diagram illustrating a method suitable for delivery of a gas to a tissue, according to some embodiments of the present invention.

FIG. 2 is a flowchart diagram illustrating a method suitable for delivery of a gas to a tissue, according to some embodiments of the present invention. The method is executed using system 20.

The method begins at 100 and optionally and preferably continues to 101 at which the valve 46 is switched to second state to perform purging in which the various components and gas flow lines of the system (e.g., system 52, regulator 70, and gas flow lines 80*a*, 80*b*, 80*c*, 80*d*) are washed so as to purging gas remnants and other substances (e.g., oxygen) that can react with the gas. Preferably, the purging is for a predetermined time period, e.g., at least 1 minute for at least 3 times. In some embodiments of the present invention the purging includes multiple (e.g., 3 or more) pressurize and depressurize cycles, followed by continuous flow of the purging gas. The Inventors found that such a protocol speeds up the purge and ensures that gas remnants and other substances are more effectively purged out, even from dead ended gas pathways and corners. In some embodiments of the present invention the depressurizing parts of the cycles includes application of vacuum to the gas flow lines. This can be done, for example, by temporarily connecting one of the ports of valve 46 to a vacuum source (not shown). Alternatively, valve 46 can include an additional port (e.g., a fourth port, in which case valve 46 can be a four-port valve) to which the vacuum source is connected, and the depressurizing parts of the cycles can include switching the valve to a state in which the fourth port connects to the third port 46*c*.

In some embodiments of the present invention a gas leak detection solution is applied to connections through which gas is to be delivered for visual inspection of leakage by formation of bubbles.

The method optionally and preferably continues to 102 at which the first container 26 is connected to valve 46. If the first container 26 is already connected to valve 46, operation 102 can be skipped.

The method optionally and preferably continues to 102 at which the gas flow lines are filled with the gas (e.g., gNO). Preferably, this operation is executed before connecting gas flow line 80*d* to applicator 28, and while the end of the gas flow line 80*d* is positioned at a suction inlet (e.g., of device 64 or a vacuum source), so as to prevent release of the gas to the treating room. In some embodiments of the present invention operation 103 is executed while monitoring the presence and/or concentration of the gas at the end of line 80*d*, for example, by a sensor, such as one of sensors 72, placed in proximity to the end of line 80*d*. In these embodiments, the delivery is terminated once the presence of the gas is detected and/or once the monitored concentration is above a predetermined threshold.

The method optionally and preferably continues to 104 at which oxygen or air or oxygen-enriched air is delivered to the subject, e.g., to subject's trachea, for example, by means of an oxygen mask 76 (see FIG. 1) placed on the subject's nose and/or mouth. In some embodiments of the present invention the medical practitioner preparing the subject for treatment and/or performing the treatment also wears a mask such as mask 76. The method continues to 105 at which the flow line 80*d* is connected to applicator 28. This is optionally and preferably executed after the applicator is already secured to a location near the tissue 22 and the needle 34 or sprayer already engages the tissue 22. At 106 valve 46 is again switched to its first state thereby delivering the gas to the tissue.

The method optionally and preferably proceeds to 107 at which the applicator 28 and optionally and preferably also the first container 26 are disconnected, and to 108 at which valve 46 is switched again to the second state to perform purging in which, the various components and gas flow lines of the system are washed so as to purging gas remnants and other substances (e.g., oxygen) that can react with the gas. Preferably, this operation is executed as described above with respect to operation 101. In some embodiments of the present invention at least one of operations 101 and 107 is executed while monitoring the presence and/or concentration of the gas at the end of line 80d, as further detailed hereinabove. In these embodiments, the delivery is terminated once the monitored concentration is zero or below a predetermined threshold.

The method ends at 109.

As used herein the term "about" refers to ±10% The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Prototype gNO Delivery System

Figure 3A:
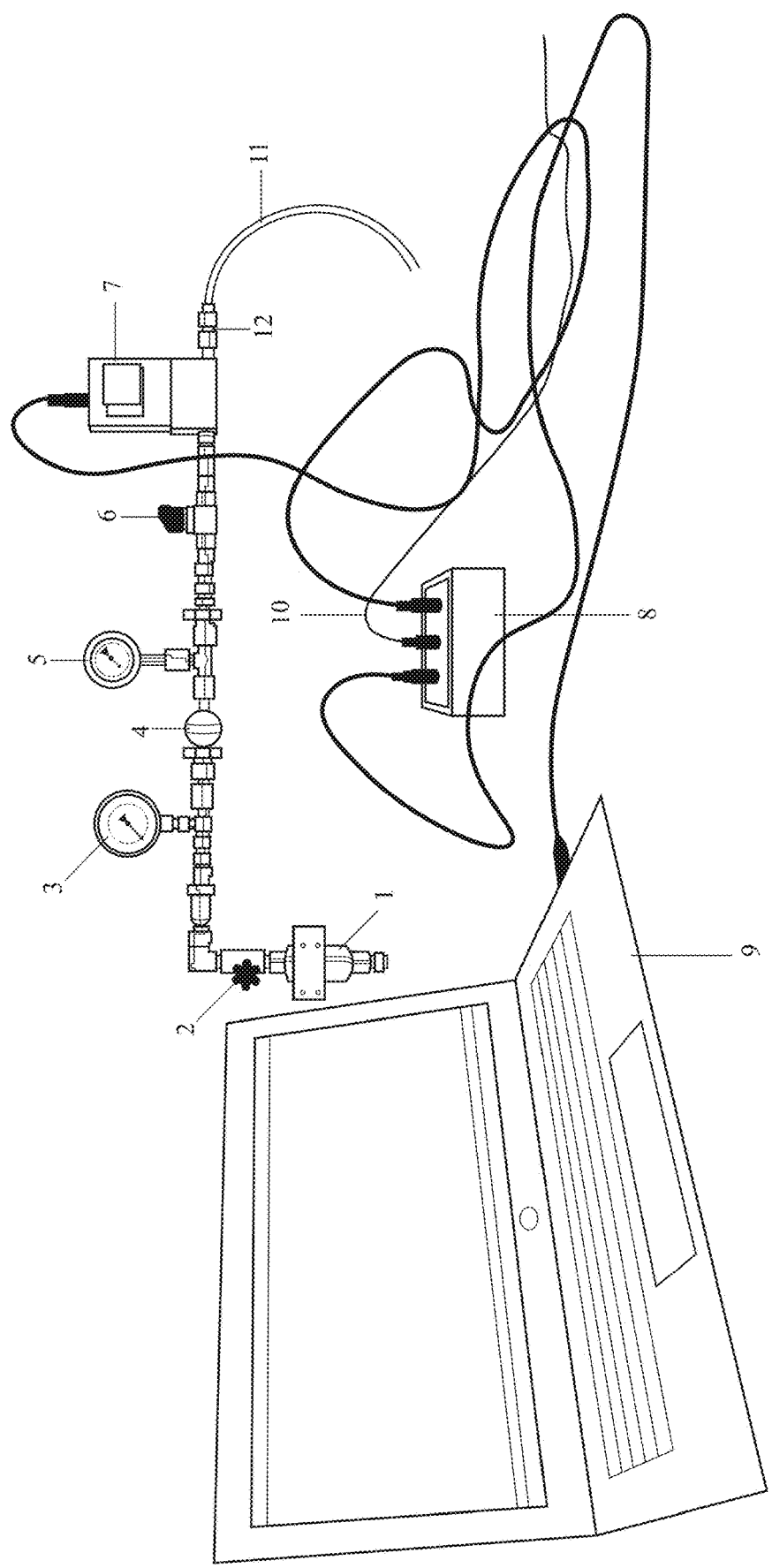
FIG. 3A is a photograph of a prototype gNO delivery system, used in experiments performed in accordance with some embodiments of the present invention.
Figure 3B:
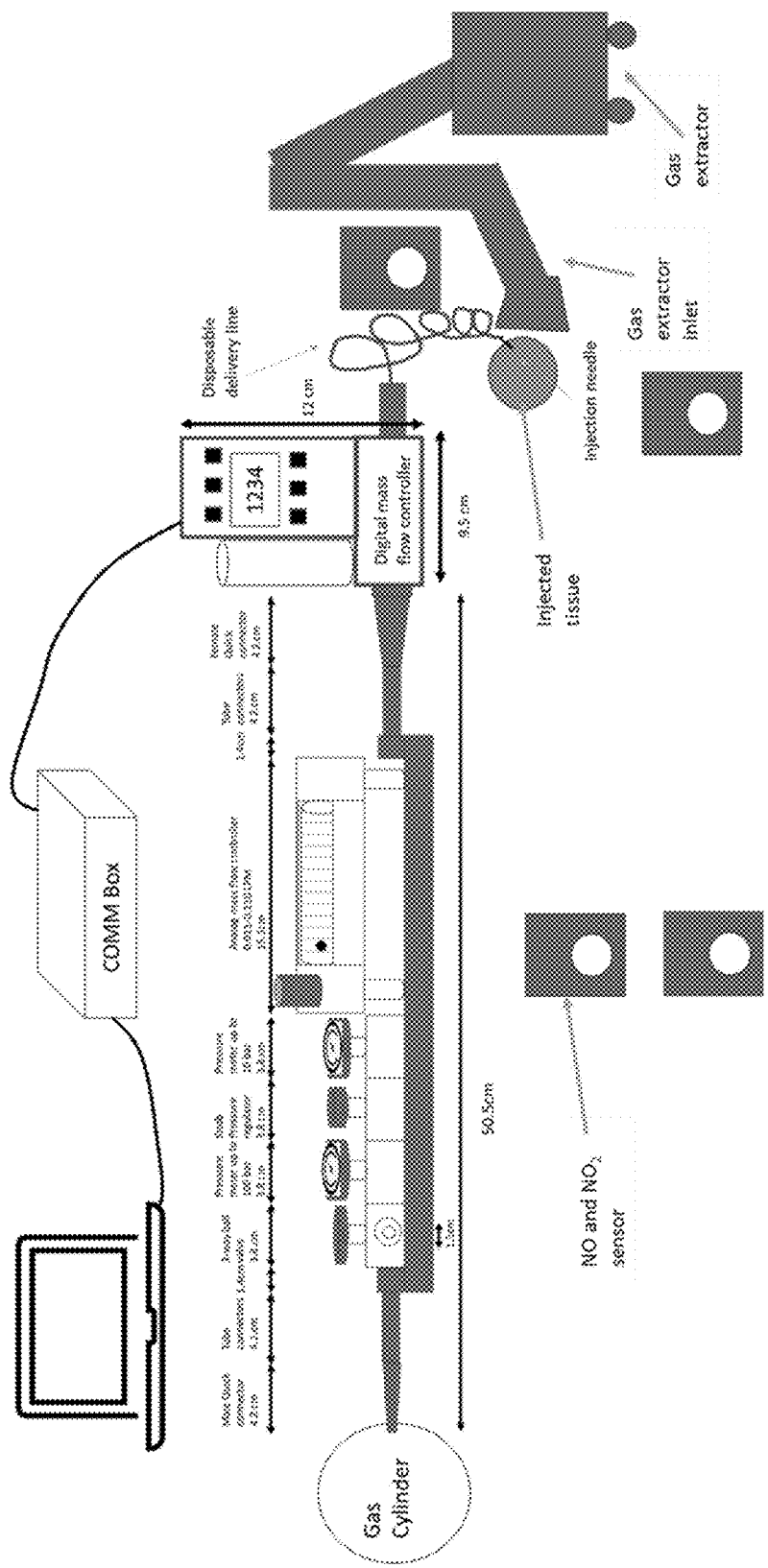
FIGS. 3B and 3C are schematic illustrations of a front view (FIG. 3B) and a top view (FIG. 3C) of the prototype system, according to some embodiments of the present invention.
Figure 3C:
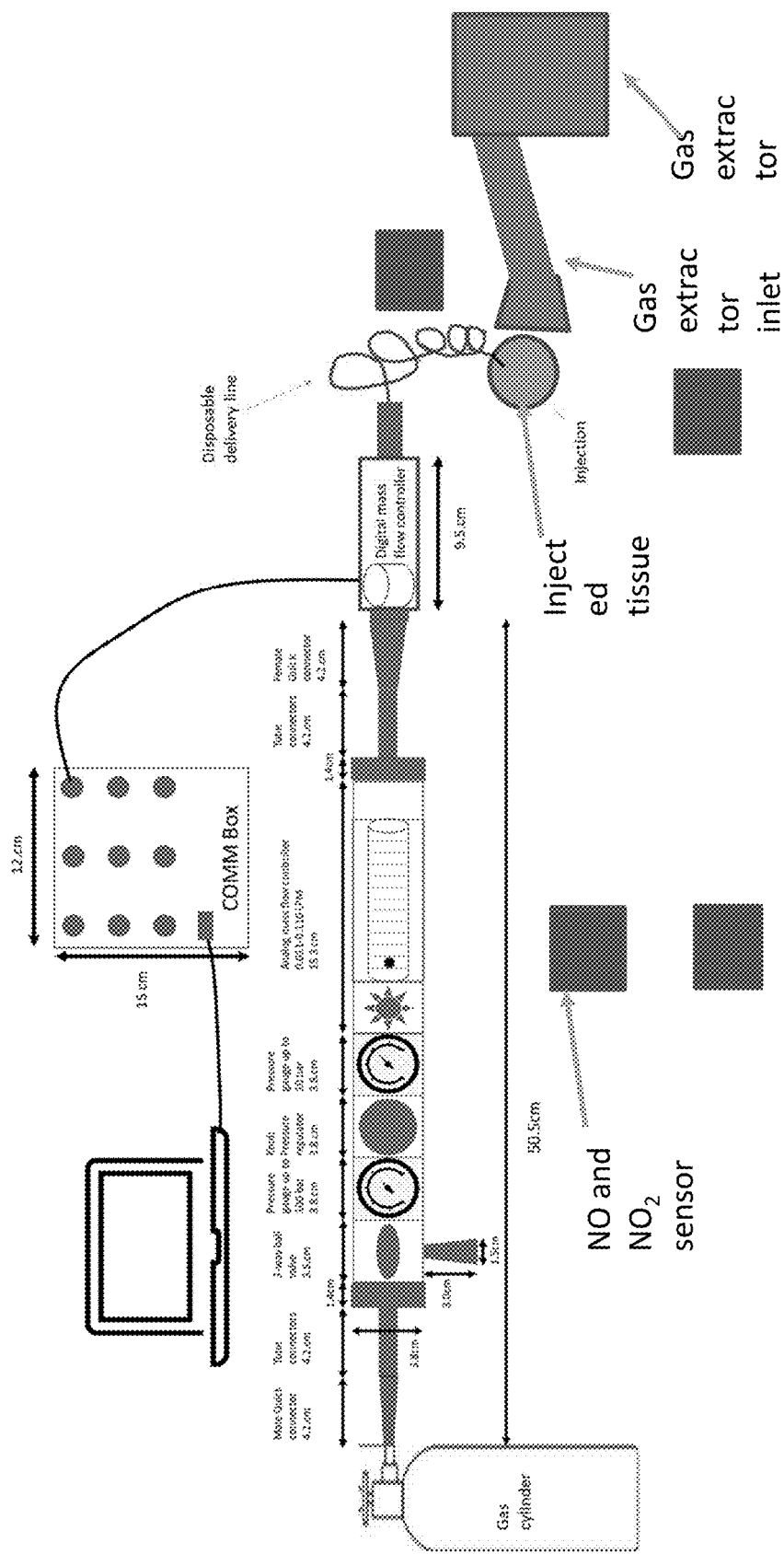

FIG. 3A is a photograph of a prototype gNO delivery system, used in experiments performed in accordance with some embodiments of the present invention. Typical dimensions of the various components of the prototype system are schematically illustrated in FIGS. 3B (front view) and 3C (side view). The prototype system has a power supply 10 and a user interface 9 for operating the system. The user interface included a laptop but can be of any other type of interface. The prototype system also comprises a communication box 8.

The system has a mini cylinder 1 in which gNO is stored under low pressure. The volume of the mini cylinder 1 can be from about 10 cc to about 3.5 L, and it contains gNO at low pressure which can be from about 1.5 bar to about 5 bar. In the performed experiments the volume of the mini cylinder 1 was 3 L.

In operation, the stem valve 2 is opened to allow gNO to leave the mini cylinder 1 and pass through a high pressure gauge 3. The gNO flows through a high flow pressure regulator 4, a low pressure gauge 5, a ball valve 6, and a digital flow controller 7. The gNO gas flow continues past the flow controller 7 to a gas outlet 12, where it connects to nitric oxide applicator 11. The applicator 11 applied the gNO to the tumor and/or metastases.

In the prototype system, the nitric oxide applicator 11 comprises a cannula that ends in either a needle or a sprayer. The needle can be any suitable needle for delivering gNO to a tissue, in vivo, including, but not limited to, a perforated spray needle, non-perforated and non-spray needle, umbrella needle, or other needles. The needle can optionally be nano size, micron size or macro size needles. In the performed experiments the needle was a 23G non-perforated and non-spray needle.

Example 2

Exemplified Gas Applicators and Treatment Protocols

Following is a description of several gas applicators which can be used as applicator 28, and treatment protocols which can be employed according to some embodiments of the present invention.

Figure 4A:
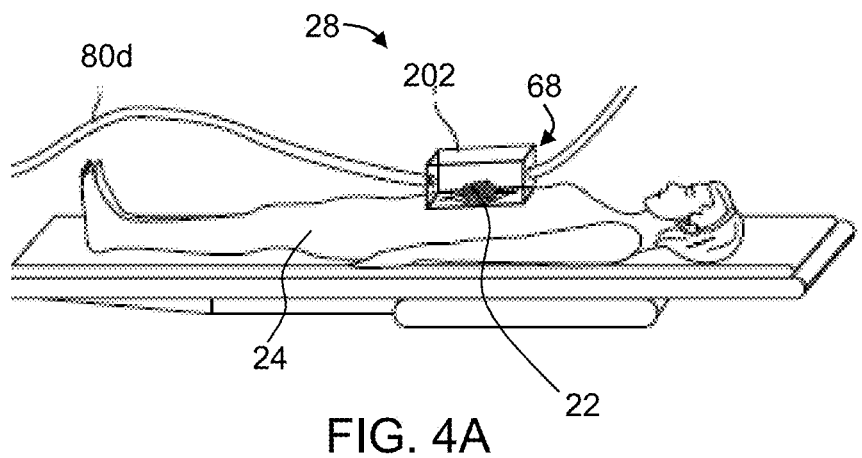
FIGS. 4A, 4B, 4C, 4D, 4F and 4G are schematic illustrations of a gas applicator, according to some embodiments of the present invention.

FIG. 4A is a schematic illustration of an embodiment in which applicator 28 comprises a box 202. Tumor 22 is placed inside box 202 before gas delivery. The gas is then delivered to box 202 while excessive gas is evacuated by suctioning through suction inlet 68 to an evacuation system that is preferably connected to the medical center pipe to allow releasing of the gas outside (not shown).

Figure 4B:
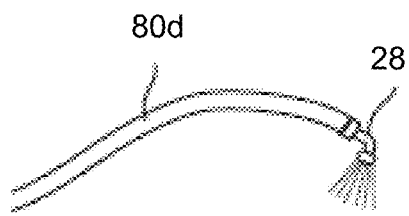

FIG. 4B presents a schematic illustration of an applicator 28 in embodiments in which applicator 28 is configured to deliver the gas by spraying.

Figure 4C:
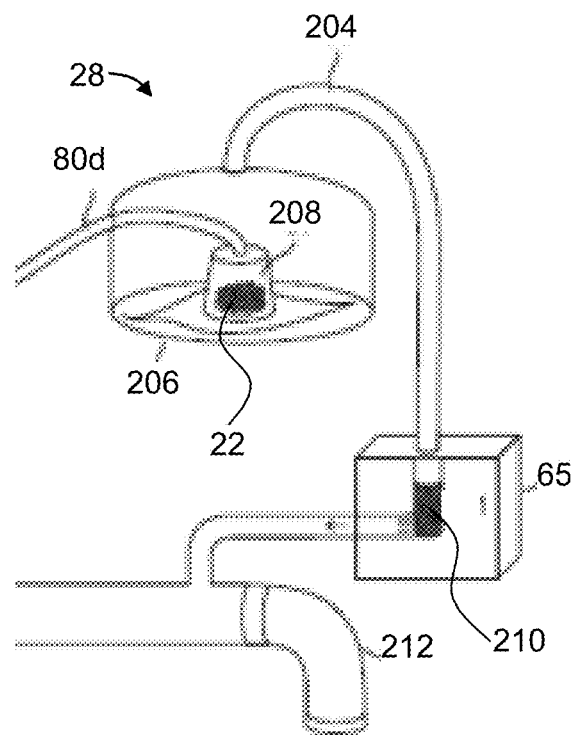

FIG. 4C presents a schematic illustration of applicator 28 in embodiments in which applicator 28 comprises a cap 208. The gas can be delivered directly to the outer layer of tissue 22 by cap 208 that covers tumor 22 and is placed inside a sealed outer cap 206 that is connected to a flow line 204 through which excessive gas is evacuated by suctioning and is optionally and preferably also filtered by filter 65, which may include a tube filled with a substance 210 such as soda lime, filtering out gNO and optionally also $NO_2$ from the gas mixture coming out of the tumor cap 208 to release clean air. Typically, the clean air is released into the pipes 212 of the medical center.

Figure 4D:
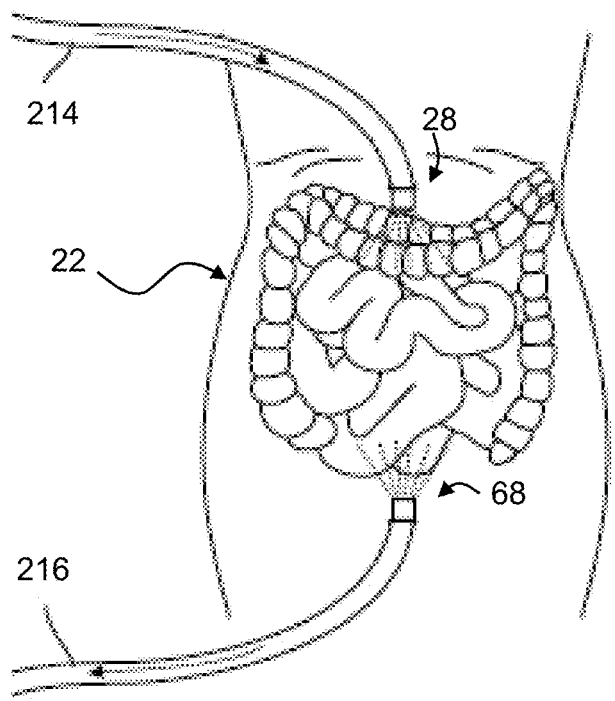

FIG. 4D presents a schematic illustration of applicator 28 in embodiments in which applicator 28 comprises a gas releasing laparoscope 214 for delivering the gas directly to the tumor 22. An evacuation flow line 216 having suction inlet 68 at its distal end can immediate remove of excessive gas at the surroundings of the tissue 22. Such a configuration is exemplified in FIG. 4D with spraying applicator but can alternatively use a needle or any other delivering device mounted at the distal end of laparoscope 214.

Figure 4E:
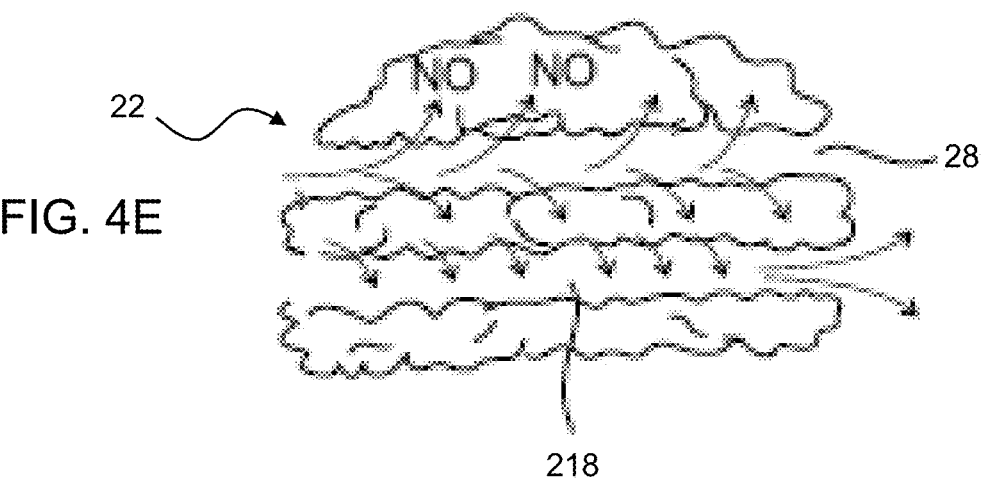

FIG. 4E presents a schematic illustration of applicator 28 in embodiments in which applicator 28 comprises a gas delivery channel introducible into the tumor 22. To control the intra-tumoral pressure, excessive gas can be evacuated through an intra-tumoral gas-scavenging channel 218 that can be connected to a filter as further detailed hereinabove.

Figure 4F:
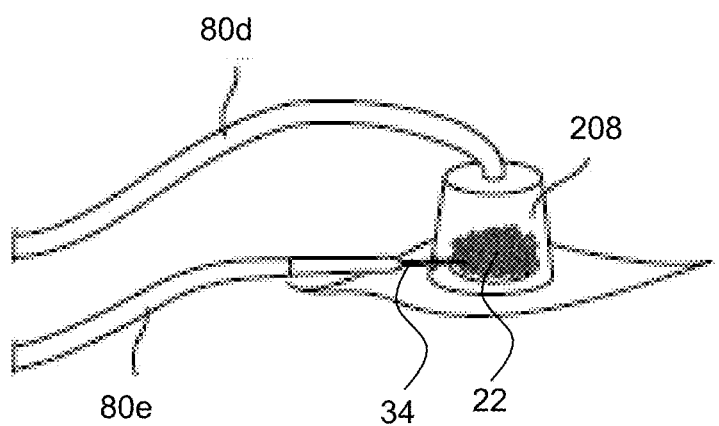

FIG. 4F presents a schematic illustration of applicator 28 in embodiments in which applicator 28 comprises the cap 208 as well as the needle 34. In these embodiments, system 20 optionally and preferably comprises two flow lines 80d and 80e (or a single split flow line) to deliver the gas both to the cap 208 and to the needle 34, thereby increasing the number of cells that are exposed to the gas.

Figure 4G:
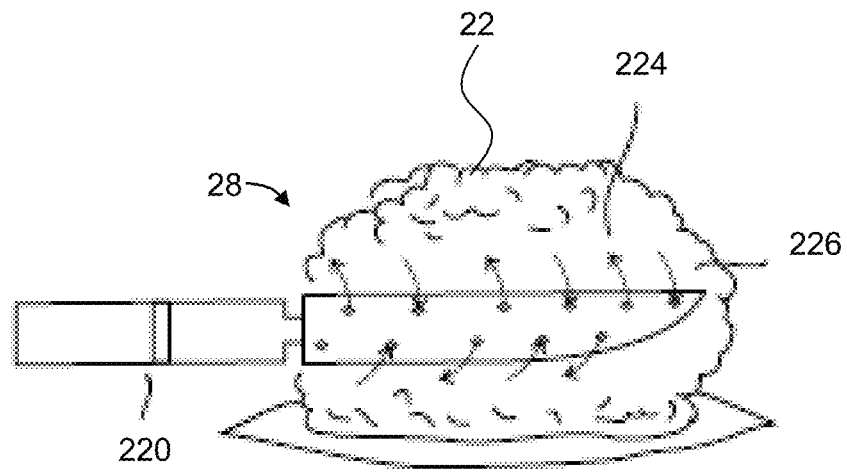

FIG. 4G presents a schematic illustration of applicator 28 in embodiments in which applicator 28 comprises a gas releasing scalpel having a holder 220, and gas releasing pores 224 that are fluid communication with flow line 80d (not shown). These embodiment combine treatment by gas with a surgical procedure, in which tumor 22 is excised while applying the gas. In some embodiments of the present invention applicator 28 also comprises gas evacuation pores 226 that are connected to suctioning device 64 (not shown). The suctioning of the gas can be done in a pulsed or continuous manner.

Figure 5A:
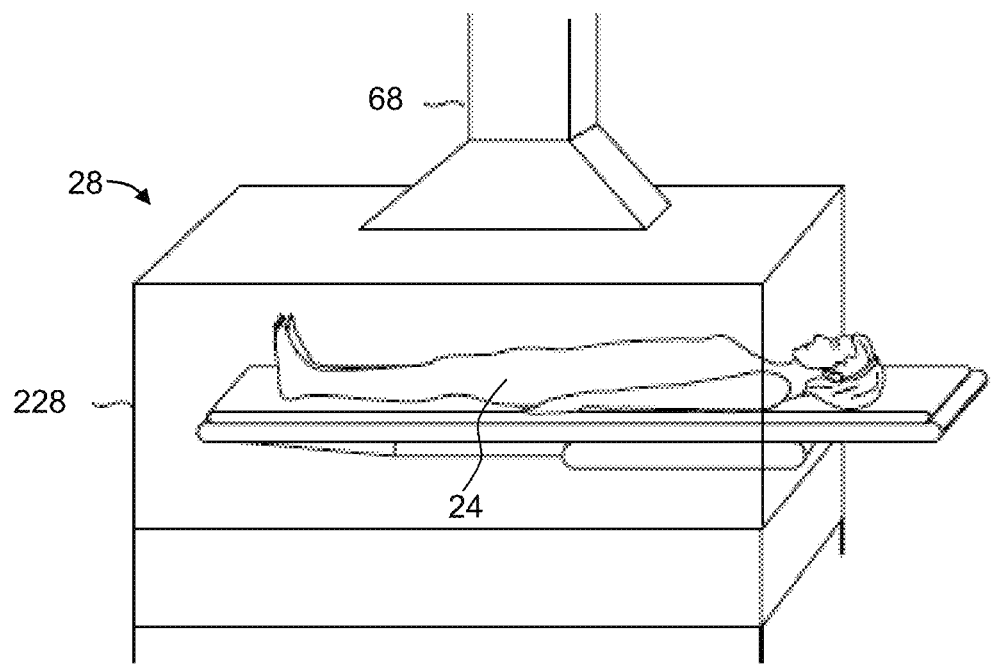
FIGS. 5A and 5B are schematic illustrations of embodiments of the present invention which employ a hood.

FIG. 5A presents a schematic illustration of applicator 28 in embodiments in which applicator 28 comprises a chemical hood 228 sized to receive a portion of the body of subject 24. Suction inlet 68 is optionally and preferably connected to hood 228 to evacuate the gas and optionally reaction products as further detailed hereinabove.

Figure 5B:
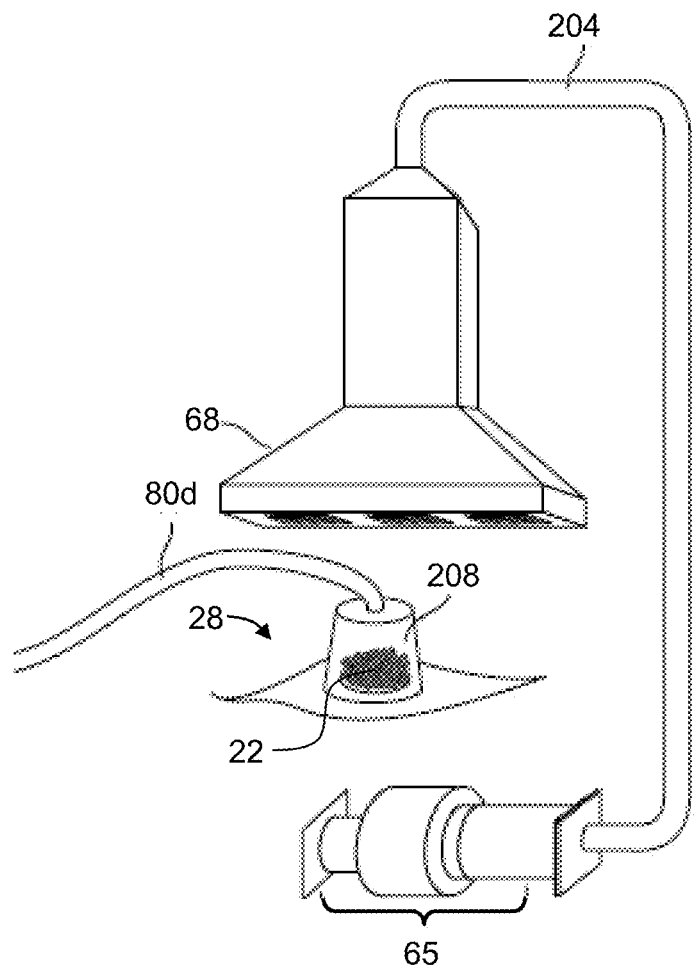

FIG. 5B presents a schematic illustration of a configuration in which applicator 28 comprises cap 208, as further detailed hereinabove, and the suction inlet 68 is in the form of a chemical hood placed directly above cap 208, and is connected to flowline 204, which in turn is connected to a pump (not shown) via filter 65 which can include multiple filtering elements.

Figure 5C:
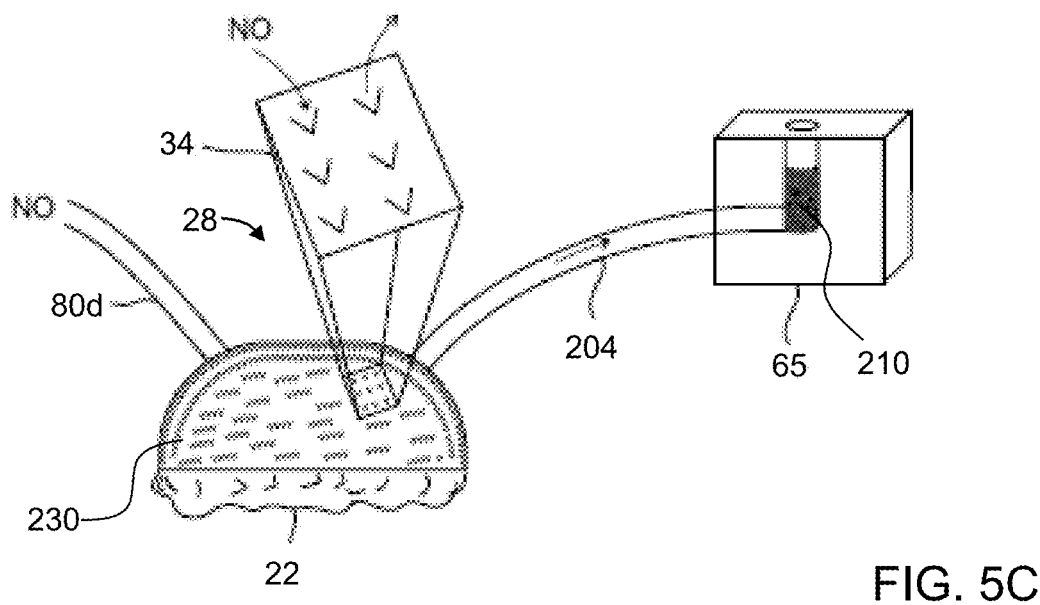
FIGS. 5C and 5D are schematic illustrations of a gas applicator in embodiments in which the applicator comprises a patch (FIG. 5C), and in embodiments in which the applicator comprises a perforated spray intra-tumoral needle.

FIG. 5C presents a schematic illustration of applicator 28 in embodiments in which applicator 28 comprises a patch 230 having a plurality of needles 34 (shown in an enlarged form) on its surface. Needles 34 include gas input needles and gas output needles for a rapid clear up of excessive gas. The output needles are connected to flow line 204 that is connected to a pump (not shown) via filter 65.

Figure 5D:
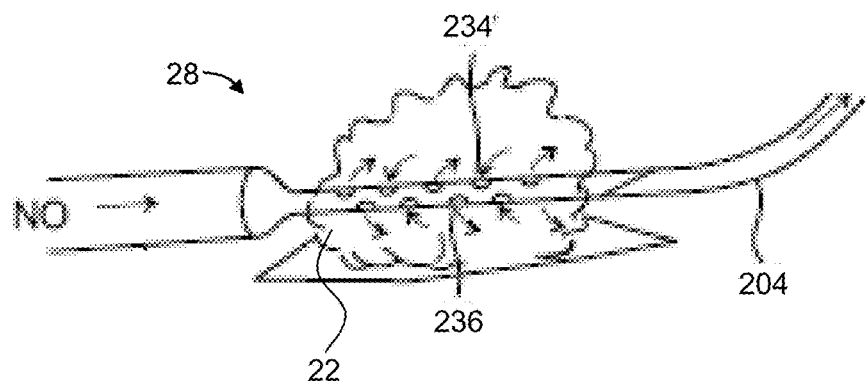

FIG. 5D presents a schematic illustration of applicator 28 in embodiments in which applicator 28 comprises a perforated spray intra-tumoral needle with input pores 234 and output pores 236. Suctioning of the gas and reaction products is performed via flow line 204, which may be directly connected to the perforated spray intra-tumoral needle at its distal end.

Figures 6A, 6B, 6C:
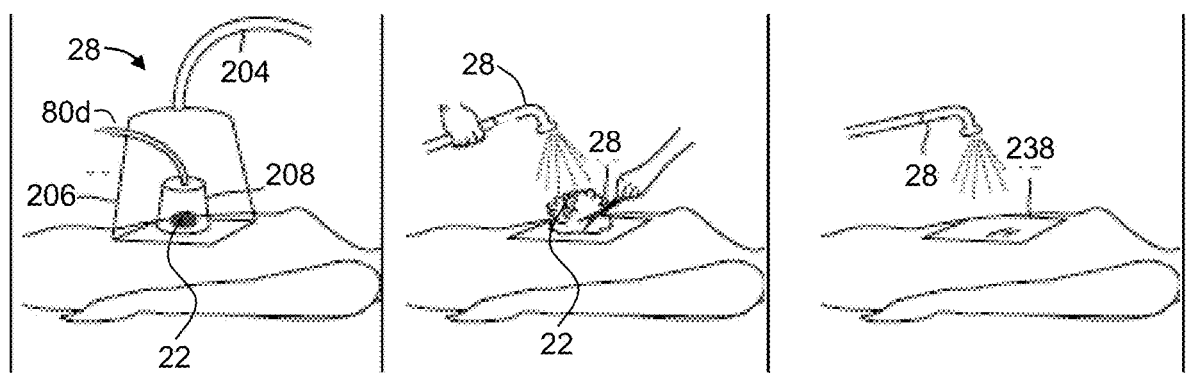
FIGS. 6A, 6B and 6C are a schematic illustrations of an exemplary procedure in which local administration of gas is used in combination with a surgical procedure, according to some embodiments of the present invention.

FIGS. 6A-C are a schematic illustrations of an exemplary procedure in which the local administration of the gas is used in combination with a surgical procedure (tumor excision or resection). In FIG. 6A, gas is delivered to the tumor site with capping 208. In FIG. 6B, during the surgical procedure, at least a portion of tumor 22 is exposed and the gas is applied, for example, by spraying. The operated tumor 22 is being exposed to the gas while being excised by a scalpel, which in some embodiments of the present invention can be, the applicator 28 when embodied as a gas releasing scalpel as further detailed hereinabove. In FIG. 6C, post-surgery, the operated site 238 (e.g., after removal of tumor 22) is exposed again to the gas, for example, by spraying using applicator 28.

Figure 7:
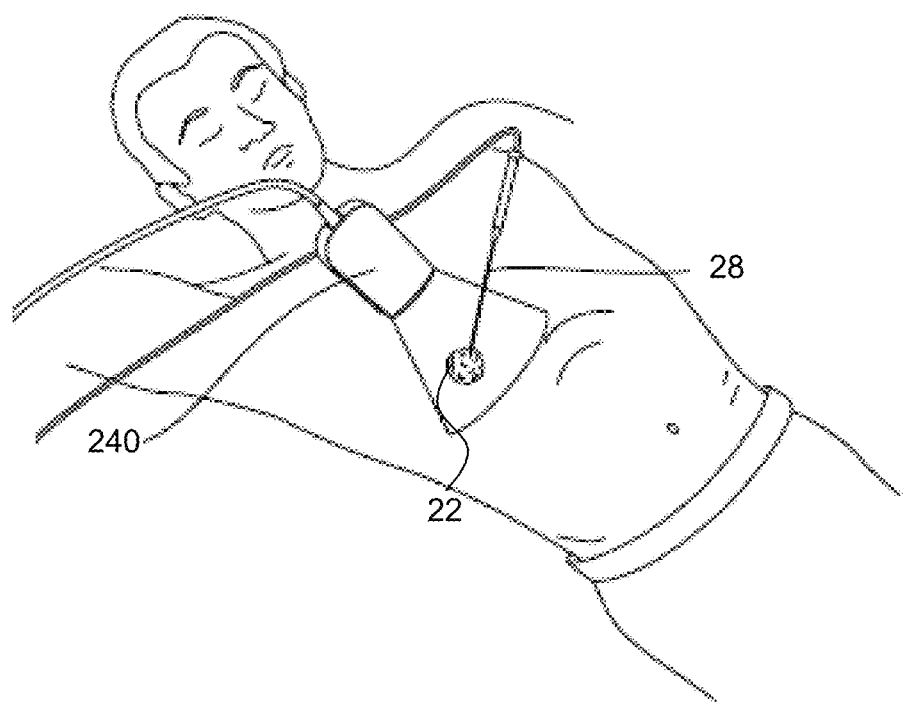
FIG. 7 is a schematic illustration of an exemplary configuration which involves identifying a presence of tumor by imaging, and applying gas treatment to the tumor, according to some embodiments of the present invention.

FIG. 7 presents a schematic illustration of an exemplary configuration which involves identifying a presence of tumor 22 with an imaging apparatus 240 and locally administering to the tumor the gas using applicator 28. According to some of any of the embodiments described herein, the imaging apparatus employs a technique such as, but not limited to, computed tomography (CT), ultrasound (US), magnetic resonance imaging (MRI), and any other imaging technique, and may be used, during any known procedure such as laparoscopy, bronchoscopy and others.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

We claim:

1. A system for delivery of gas to a tissue, the system comprising:
a first container containing the gas;
an applicator having a distal end arranged to deliver the gas to the tissue;
a second container containing a purging gas;
a three-port valve having a first port for receiving the gas from said first container, a second port for receiving the purging gas from said second container, and a third port in fluid communication with said applicator, said valve being switchable between a first state at which said first port fluidly connects to said third port, and a second state at which said second port fluidly connects to said third port;
a flow control system for controlling flow of gas exiting said third port; and
a computerized controller for automatically controlling said flow control system, according to at least one of: a predetermined gas flow rate, a predetermined total amount of the gas flowing through said flow control system, and a predetermined total amount of time in which said gas flows through said flow control system;
wherein said flow control system comprises a digital flow controller configured for controlling flow in a closed loop according to a pseudo-derivative tuning coefficient and a proportional tuning coefficient, and
wherein said computerized controller is configured to receive, via a user interface, input flow rate of the gas, and to automatically select said tuning coefficients based on said input.

2. The system according to claim 1, wherein said applicator and said first container are disposable.

3. The system according to claim 1, comprising a suctioning device arranged to apply suction at a vicinity of said distal end of said applicator to withdraw excess gas exiting said distal end.

4. The system according to claim 3, comprising a filter for filtering said withdrawn excess gas.

5. The system according to claim 1, wherein said digital flow control system comprises a flow controller and a flow limiter for limiting flow rate of the gas before entering said flow controller.

6. The system according to claim 1, comprising an adjustable pressure regulator, in fluid communication with said third port of said valve, and being configured for maintaining a pressure which is below a predetermined threshold when said valve assumes said first state, and a pressure which is above said predetermined threshold when said valve assumes said second state.

7. The system according to claim 1, wherein said digital flow controller is configured for controlling said flow in said closed loop also according to an integral tuning coefficient, and said computerized controller is configured to automatically select said integral tuning coefficient based on said input.

8. The system according to claim 1, wherein said computerized controller is configured to select for said proportional tuning coefficient a value which is higher for lower input flow rates than for higher input flow rates.

9. The system according to claim 1, wherein said computerized controller is configured to select for said pseudo-derivative tuning coefficient a value which is lower for lower input flow rates than for higher input flow rates.

10. The system according to claim 1, further comprising an arrangement of sensors, the arrangement of sensors configured to be distributed in a treatment room and to sense said gas within said treatment room and configured to issue an alert signal when a level of the gas is above a respective predetermined threshold.

11. The system according to claim 1, further comprising an arrangement of sensors, the arrangement of sensors configured to be distributed in a treatment room to sense said gas within said treatment room, wherein said computerized controller is configured to receive sensing signals from said sensors and issue an alert signal when a level of the gas is above a respective predetermined threshold.

12. The system according to claim 1, wherein said first container has a volume of less than 100 cc.

13. The system according to claim 1, wherein the gas is gaseous nitric oxide (gNO).

14. The system according to claim 1, wherein the purging gas is nitrogen or argon.

15. A method for delivery of gas to a tissue, the method comprising:
in the system according to claim 1:
connecting said first container to said valve;
switching said valve to said first state, thereby delivering the gas to the tissue;
disconnecting said applicator and said first container; and
switching said valve to said second state, thereby purging at least said flow control system.

16. The method according to claim 15, comprising applying suction at a vicinity of said distal end of said applicator to withdraw excess gas exiting said distal end.

17. The method according to claim 15, being executed by an operator, and comprising delivering air or oxygen or oxygen-enriched air to said operator.

18. The method according to claim 15, wherein the tissue is a tissue of a subject, and the method comprising delivering air or oxygen or oxygen-enriched air to said subject.

19. The method according to claim 15, wherein said purging comprises applying multiple pressurize and depressurize cycles, followed by continuous flow of said purging gas.

20. A method for delivery of gas to a tissue, the method comprising:
in the system according to claim 2:
connecting said first container to said valve;
switching said valve to said first state, thereby delivering the gas to the tissue;
disconnecting said applicator and said first container; and
switching said valve to said second state, thereby purging at least said flow control system.

21. The method according to claim 20, comprising applying suction at a vicinity of said distal end of said applicator to withdraw excess gas exiting said distal end.

* * * * *